(12) United States Patent
Smith et al.

(10) Patent No.: US 10,857,006 B2
(45) Date of Patent: Dec. 8, 2020

(54) LOWER LEG PROSTHETIC SYSTEMS AND DEVICES

(71) Applicant: PURDUE RESEARCH FOUNDATION, West Lafayette, IN (US)

(72) Inventors: Haley Elizabeth Smith, Dallas, TX (US); Jennifer Anne Boehm, Cincinnati, OH (US); Rachel Nicole Berry, Naperville, IL (US); Sami Imad Labban, Princeton Junction, NJ (US); Allison Jean Gleason, Springfield, IL (US); Eric Allen Nauman, West Lafayette, IN (US); Quinton James Lasko, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 167 days.

(21) Appl. No.: 15/614,987

(22) Filed: Jun. 6, 2017

(65) Prior Publication Data
US 2018/0125680 A1    May 10, 2018

Related U.S. Application Data

(60) Provisional application No. 62/345,969, filed on Jun. 6, 2016.

(51) Int. Cl.
*A61F 2/50* (2006.01)
*A61F 2/66* (2006.01)
*A61F 2/76* (2006.01)

(52) U.S. Cl.
CPC .............. *A61F 2/66* (2013.01); *A61F 2/5044* (2013.01); *A61F 2/6607* (2013.01); *A61F 2/76* (2013.01);
(Continued)

(58) Field of Classification Search
CPC .. A61F 2/66; A61F 2/6607; A61F 2/76; A61F 2002/6614; A61F 2002/6621;
(Continued)

(56) References Cited

U.S. PATENT DOCUMENTS

| 78,048 A | * | 5/1868 | Briody | A61F 2/6607 623/50 |
| 434,618 A | * | 8/1890 | Wintermute | A61F 2/6607 623/49 |

(Continued)

*Primary Examiner* — Christie L Bahena
(74) *Attorney, Agent, or Firm* — Hartman Global IP Law; Gary M. Hartman; Domenica N. S. Hartman

(57) ABSTRACT

Systems and devices for use as lower leg prosthetic devices that include a foot portion having anterior and posterior ends and a first surface having a protrusion that protrudes therefrom adjacent the posterior end of the foot portion, has a semispherical or hemispherical surface with a passage therethrough extending laterally relative to the foot portion. The systems and devices further include a toe portion pivotally coupled to the anterior end of the foot portion, and a plate portion configured to couple to an attachment device and thereby be functionally secured to a user. The plate portion has a recess configured to couple with the protrusion of the foot portion. A cylindrical rod is located within the lateral passage of the protrusion and has ends protruding therefrom on oppositely-disposed of the protrusion. The plate portion is pivotally coupled to the ends of the rod on oppositely-disposed lateral sides of the protrusion.

17 Claims, 18 Drawing Sheets

(52) U.S. Cl.
CPC ............ *A61F 2002/5007* (2013.01); *A61F 2002/5009* (2013.01); *A61F 2002/5043* (2013.01); *A61F 2002/6614* (2013.01); *A61F 2002/6621* (2013.01); *A61F 2002/6657* (2013.01)

(58) Field of Classification Search
CPC ...... A61F 2002/6628; A61F 2002/6635; A61F 2002/6642; A61F 2002/665; A61F 2002/6657; A61F 2002/6664; A61F 2002/6671; A61F 2002/6678; A61F 2002/6685; A61F 2002/66; A61F 2002/6692; Y10T 403/32909; F16C 11/069
See application file for complete search history.

(56) References Cited

U.S. PATENT DOCUMENTS

| | | | | | |
|---|---|---|---|---|---|
| 515,691 | A | * | 2/1894 | Kane | A61F 2/6607 623/47 |
| 804,207 | A | * | 11/1905 | Bunderle | A61F 2/60 623/33 |
| 1,937,870 | A | * | 12/1933 | Carnes | A61F 2/66 623/49 |
| 4,089,072 | A | * | 5/1978 | Glabiszewski | A61F 2/60 623/27 |
| 4,180,872 | A | * | 1/1980 | Chaikin | A61F 2/66 12/142 EV |
| 5,116,383 | A | * | 5/1992 | Shorter | A61F 2/66 623/49 |
| 5,913,902 | A | * | 6/1999 | Geible | A61F 2/66 623/52 |
| 6,187,052 | B1 | * | 2/2001 | Molino | A61F 2/6607 623/47 |
| 6,596,029 | B1 | * | 7/2003 | Gramnas | A61F 2/66 623/55 |
| 7,819,926 | B1 | * | 10/2010 | Longino | A61F 2/66 623/47 |
| 9,615,944 | B2 | * | 4/2017 | Will | A61F 2/60 |
| 2003/0065403 | A1 | * | 4/2003 | Meyer | A61F 2/76 623/38 |
| 2003/0163206 | A1 | * | 8/2003 | Yasui | A61F 2/6607 623/24 |
| 2005/0033451 | A1 | * | 2/2005 | Aigner | A61F 2/66 623/53 |
| 2011/0182654 | A1 | * | 7/2011 | Hu | F16D 3/16 403/123 |
| 2017/0058945 | A1 | * | 3/2017 | James | B63B 17/02 |

* cited by examiner

LOWER LEG PROSTHETIC SYSTEMS AND DEVICES

CROSS REFERENCE TO RELATED APPLICATIONS

This application claims the benefit of U.S. Provisional Application No. 62/345,969, filed Jun. 6, 2016, the contents of which are incorporated herein by reference.

BACKGROUND OF THE INVENTION

The present invention generally relates to prosthetic devices. The invention particularly relates to foot and ankle devices for lower leg prosthetics.

There is an estimated 185,000 lower limb amputations in the United States every year. As used herein, lower limb or lower leg refers to portions of the leg below the knee, and prosthetic devices for lower limb amputations are generally referred to as including a lower leg portion, an ankle portion, and a foot portion. The number of amputations continues to increase each year partially due to a sharp rise in diabetes. Current lower limb prosthetic devices are often bulky and unsophisticated. Many such devices generally have an "at-rest" position wherein the foot portion is about ninety degrees to the leg portion of the prosthetic device, and provide a user with little or no dorsiflexion and plantarflexion (respectively, flexion of the foot in upward and downward directions) and no pronation and supination (side-to-side (lateral) movements). For example, a SACH (solid ankle-cushioned heel) foot device as common in the art only provides ankle motion through a rubber piece in the heel of the device that compresses under loading. As used herein, the "at-rest" position is the orientation of the foot portion of a device relative to the leg portion when a user is not applying a load to the foot portion in the dorsiflexion/plantarflexion and pronation/supination directions.

Prosthetic devices offering greater ranges of ankle motion, often referred to as "smart prosthetics," have been developed to allow a user to have more control and more mobility with their prosthetic device. However, many of these devices are prohibitively expensive, tend to be heavy, and are not tailored to the needs of a specific individual. For example, the BiOM® Ankle commercially available from BionX® Medical Technologies, Inc., is a powered prosthetic device for lower limb amputees which is intended to mimic normal ankle movement during use. This device is relatively expensive and requires actuators to power the device, incurring additional weight that may cause damage to a user's native joints.

In view of the above, it can be appreciated that there are certain problems, shortcomings or disadvantages associated with the prior art, and that it would be desirable if systems and devices were available for use as lower leg prosthetic devices that were capable of providing a user with a range of ankle movement, for example, in the dorsiflexion/plantarflexion and pronation/supination directions.

BRIEF DESCRIPTION OF THE INVENTION

The present invention provides systems and devices that are suitable for use as lower leg prosthetics and capable of providing control and mobility to a user.

According to one aspect of the invention, a prosthetic device for use as a prosthetic foot includes a foot portion having anterior and posterior ends and a first surface having a protrusion that protrudes therefrom adjacent the posterior end of the foot portion, has a semispherical or hemispherical surface, and has a passage therethrough extending laterally relative to the foot portion. The device further includes a toe portion pivotally coupled to the anterior end of the foot portion, and a plate portion configured to couple to an attachment device and thereby enable the device to be functionally secured to a user. The plate portion has a recess that is configured to couple with the semispherical or hemispherical surface of the protrusion of the foot portion. A cylindrical rod is located within the lateral passage of the protrusion and has ends protruding therefrom on oppositely-disposed lateral sides of the protrusion. The plate portion is pivotally coupled to the ends of the rod on oppositely-disposed lateral sides of the protrusion.

According to another aspect of the invention, a prosthetic system for use as a lower leg prosthetic includes an attachment device configured to be secured to a user, a foot portion having anterior and posterior ends and a first surface having a protrusion that protrudes therefrom adjacent the posterior end of the foot portion, has a semispherical or hemispherical surface, and has a passage therethrough extending laterally relative to the foot portion. The device further includes a toe portion pivotally coupled to the anterior end of the foot portion, and a plate portion configured to couple to the attachment device. The plate portion has a recess that is configured to couple with the semispherical or hemispherical surface of the protrusion of the foot portion. A cylindrical rod is located within the lateral passage of the protrusion and has ends protruding therefrom on oppositely-disposed lateral sides of the protrusion. The plate portion is pivotally coupled to the ends of the rod on oppositely-disposed lateral sides of the protrusion.

Technical effects of the device and system described above preferably include the capability of promoting a user's control and mobility by enabling a relatively wide range of ankle movements, preferably including in the dorsiflexion/plantarflexion and pronation/supination directions.

Other aspects and advantages of this invention will be better appreciated from the following detailed description.

DETAILED DESCRIPTION OF THE INVENTION

Figure 1:
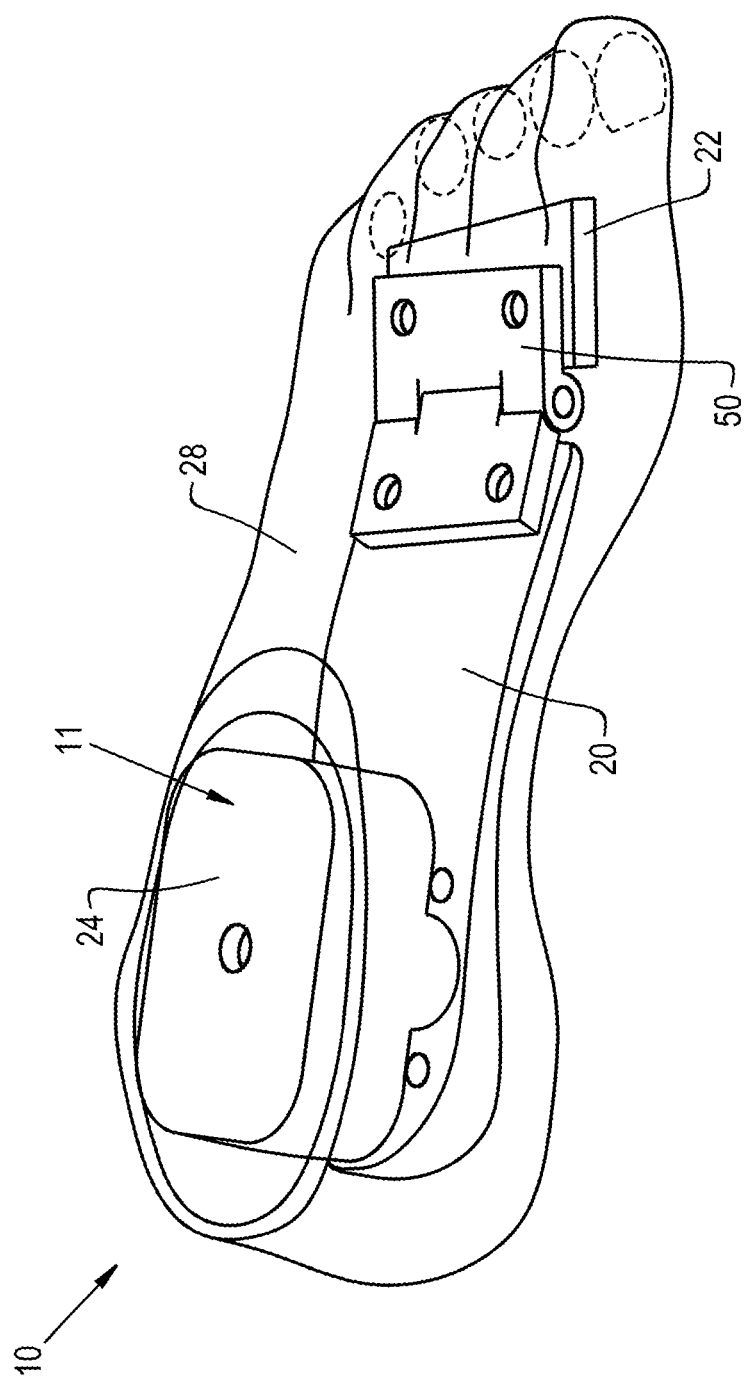
FIG. 1 is a perspective view of an ankle and foot prosthetic device in accordance with a nonlimiting first embodiment of this invention, and shows an internal structural assembly and a foot shell superimposed on the assembly to reveal the orientation of the assembly therein.
Figure 24:
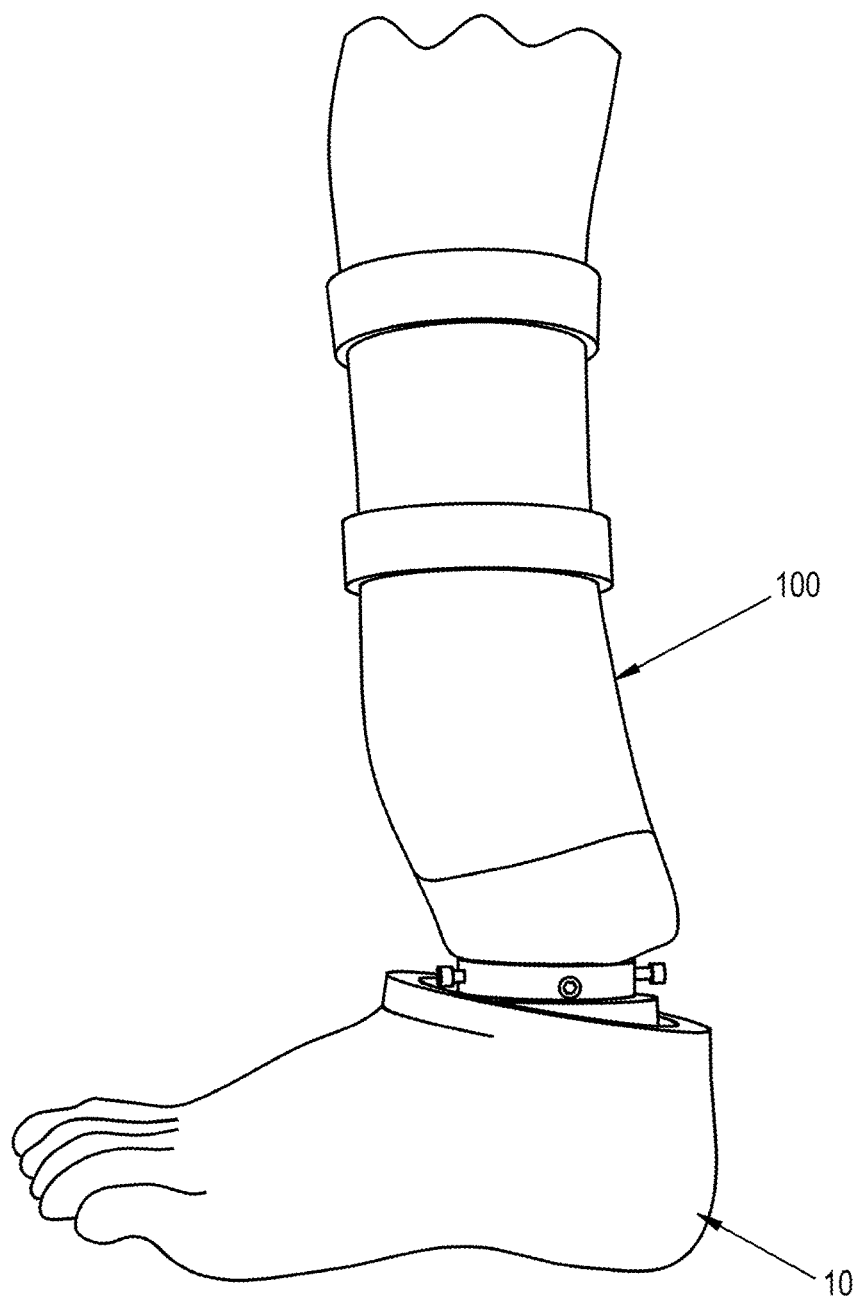
FIG. 24 represents a side view of a system comprising an ankle and foot prosthetic device coupled to a prosthetic attachment device according to a nonlimiting embodiment of the invention.

FIG. 1 represents a first nonlimiting embodiment of an ankle and foot prosthetic device 10 suitable for use by individuals as a lower limb prosthetic device or component thereof. The device 10 is capable of movement in at least four directions, including the dorsiflexion and plantarflexion directions (respectively, flexion of the foot in upward and downward directions) as well as the pronation and supination directions (side-to-side (lateral) movements). The ankle and foot prosthetic device 10 may be used as part of a system in conjunction with a prosthetic attachment device for attachment to an individual's body. For example, FIG. 24 represents a nonlimiting embodiment of a system including the device 10 with a prosthetic attachment device 100. Such attachment devices include, but are not limited to, socket attachment devices having a pylon capable of being secured to a prosthetic device with, for example, a pyramid attachment, a bolt, etc. As represented in FIGS. 1 through 4, the device 10 includes an internal structural assembly 11 that comprises a foot portion 20, a toe portion 22, a top plate 26, and a cover plate 24, and further comprises a foot shell 28 that encloses substantially the entire structural assembly 11, including its foot portion 20, toe portion 22, top plate 26, and portions of the cover plate 24.

To facilitate the description provided below of the embodiments represented in the drawings, relative terms, including but not limited to, "vertical," "horizontal," "front" (or "anterior"), "back" (or "rear" or "posterior"), "side" (or "lateral"), "forward," "backward," "upper," "lower," etc., may be used in reference to the orientation of the device 10 when worn by an individual, and therefore are relative terms that indicate the construction and use of the invention but should not be otherwise interpreted as limitations to the scope of the invention.

Figure 2:
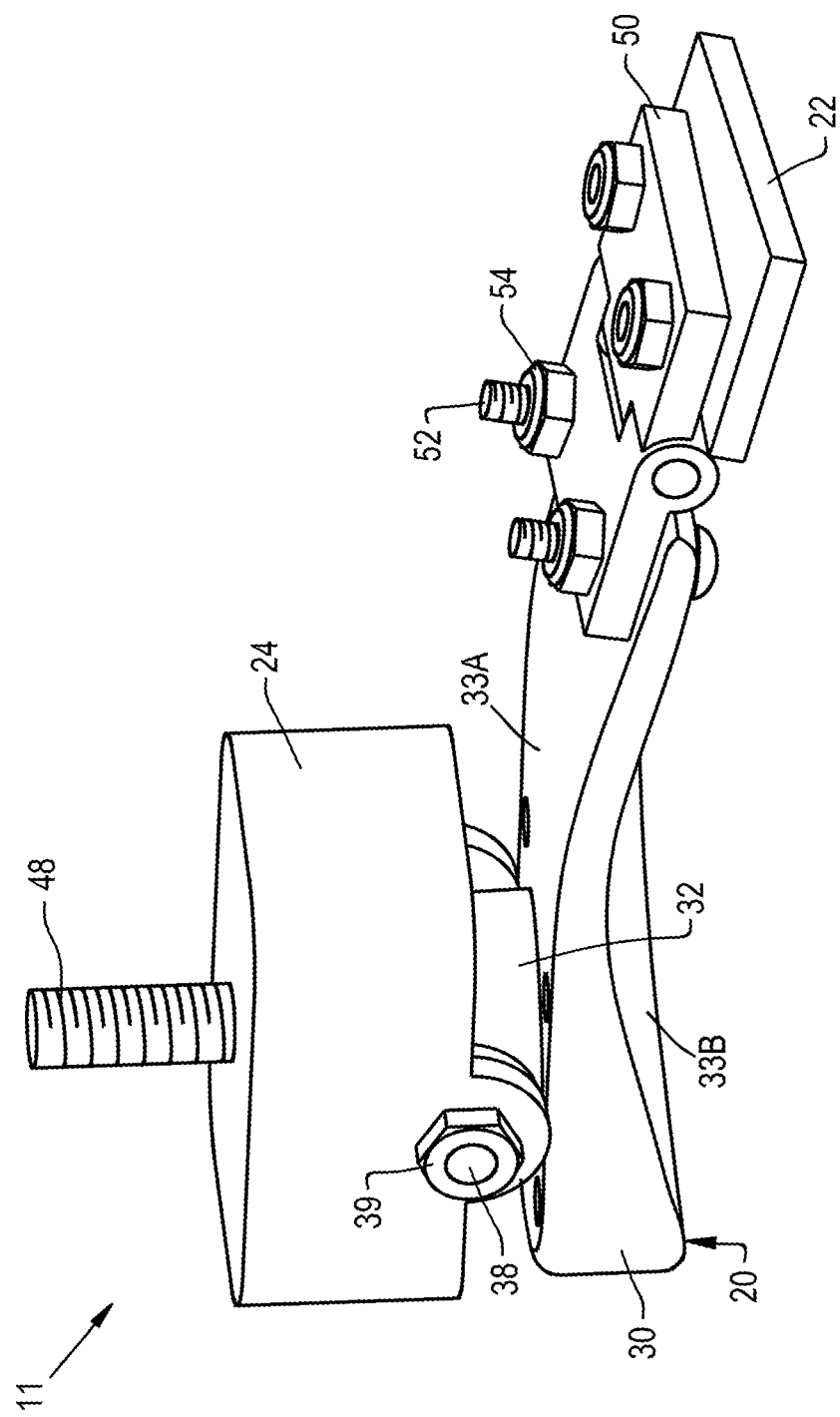
FIG. 2 is an isolated perspective view of the structural assembly of FIG. 1.
Figure 3:
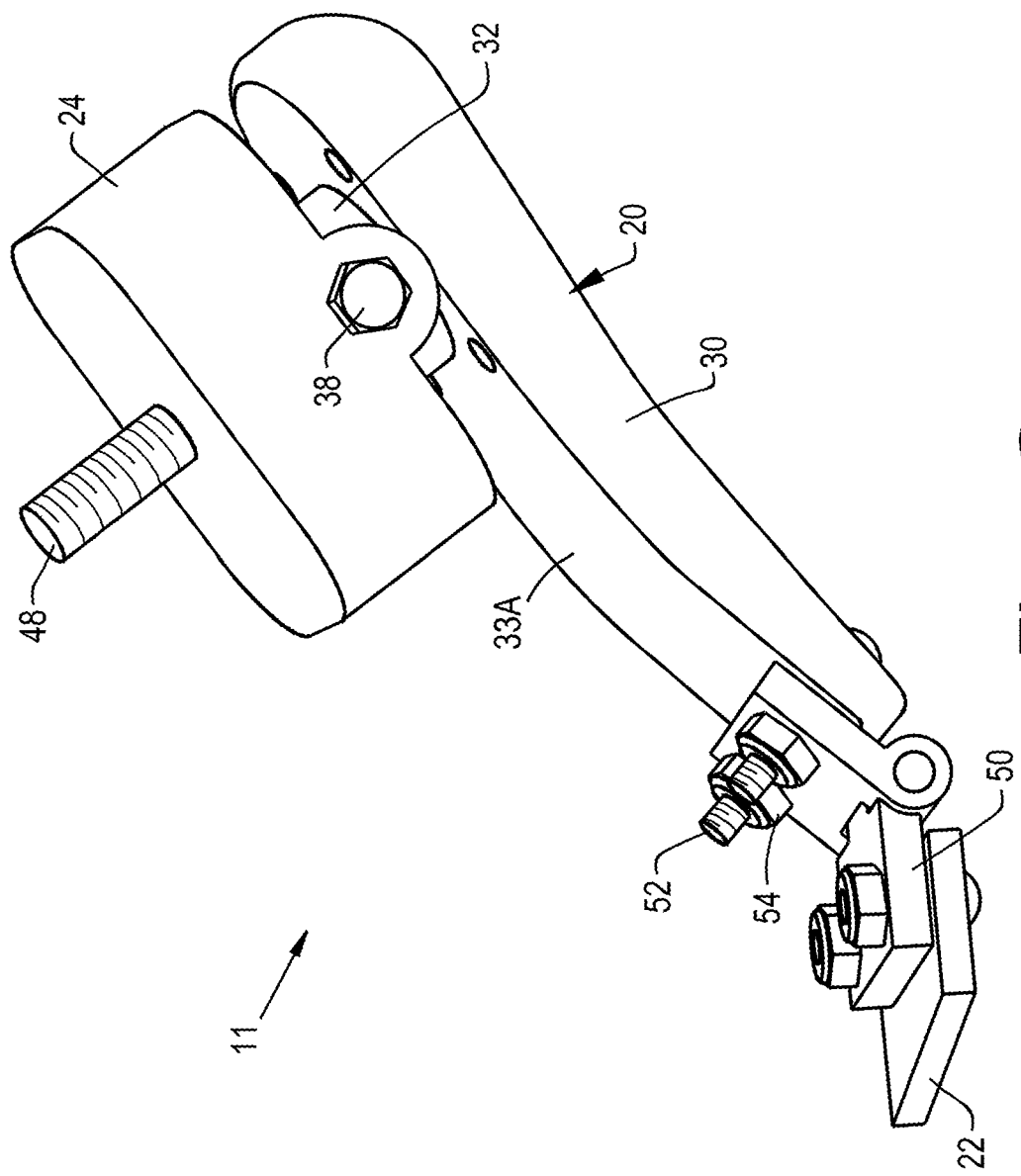
FIG. 3 is a perspective view of the structural assembly of FIG. 1 with the foot portion pivoted relative to the toe portion.
Figure 4:
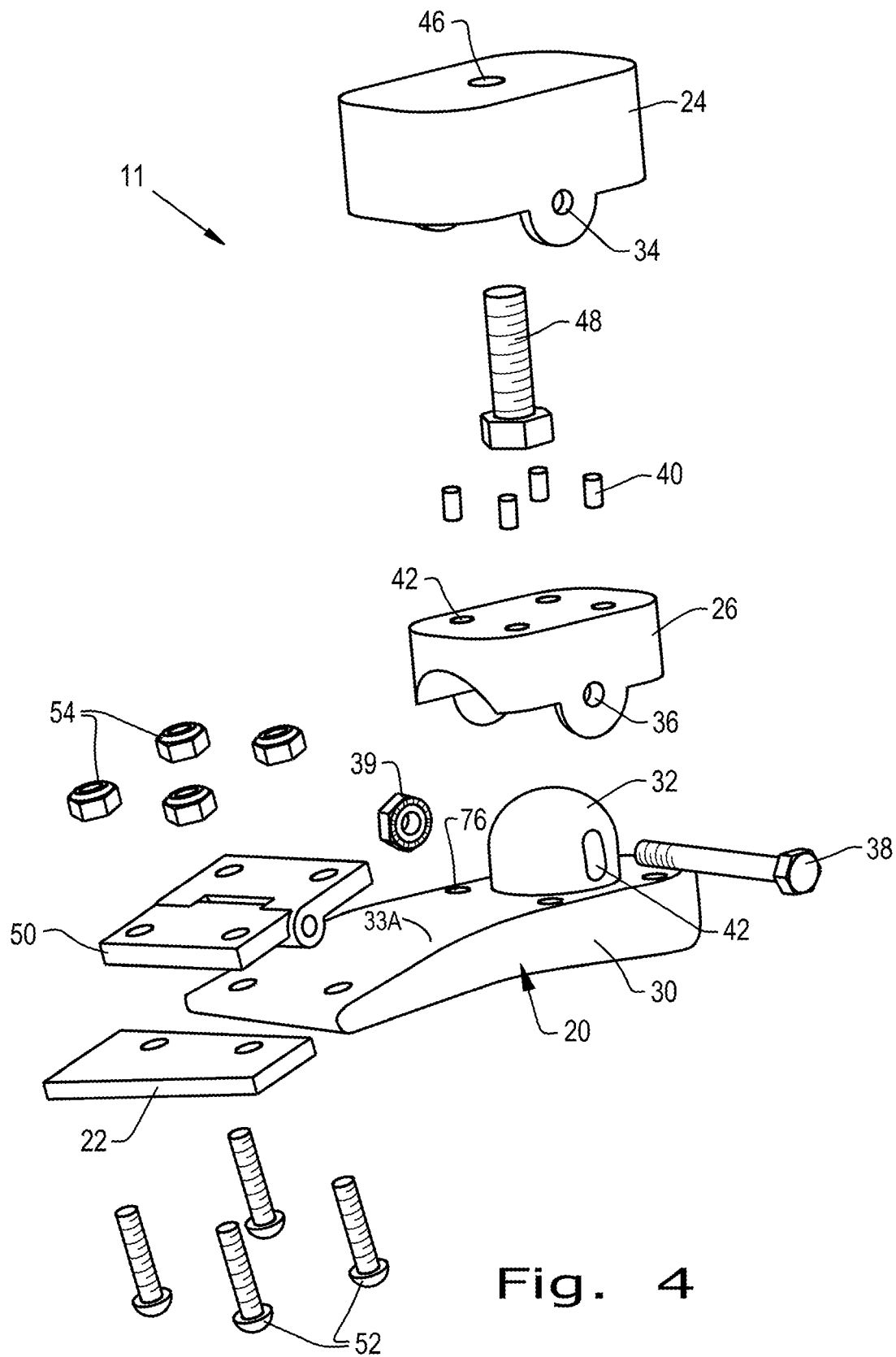
FIG. 4 is an exploded view of the structural assembly of FIG. 1.
Figure 5:
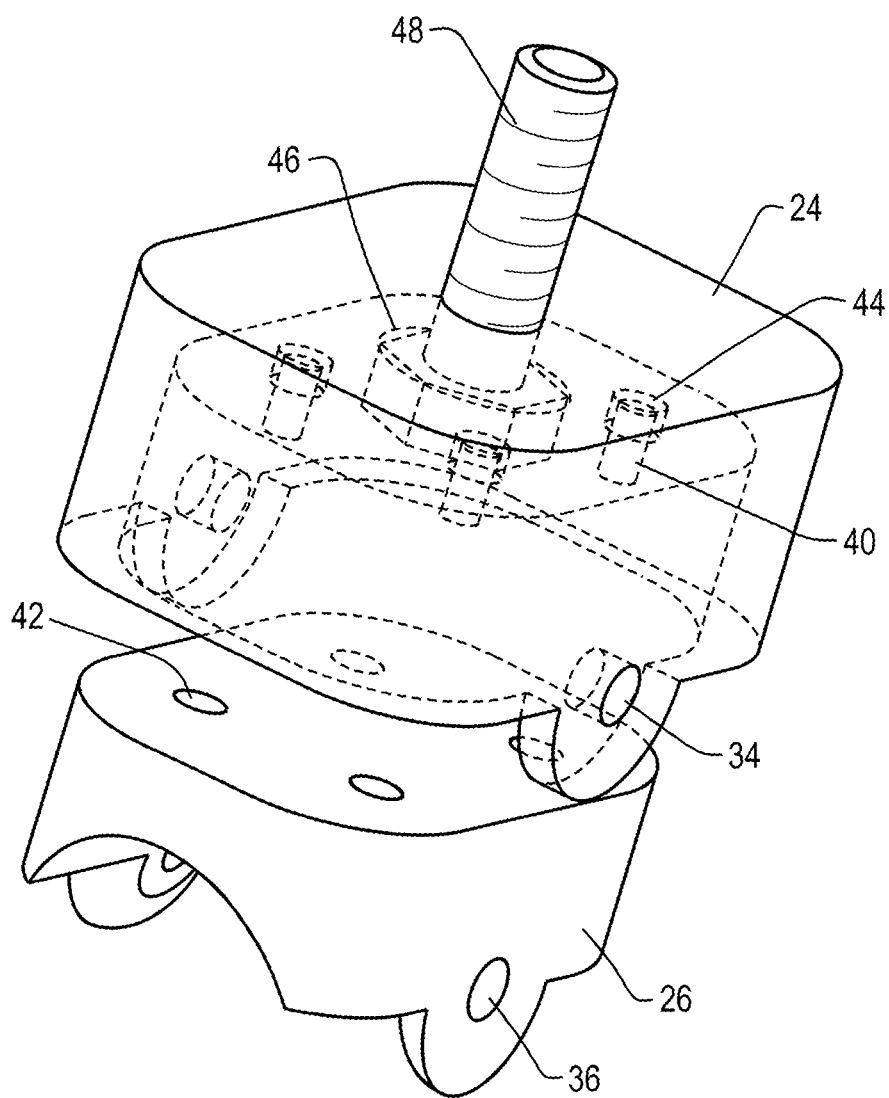
FIG. 5 is a perspective view of a top plate and cover plate of the structural assembly of FIG. 4, wherein the cover plate is transparent to expose an internal structure thereof.
Figure 6:
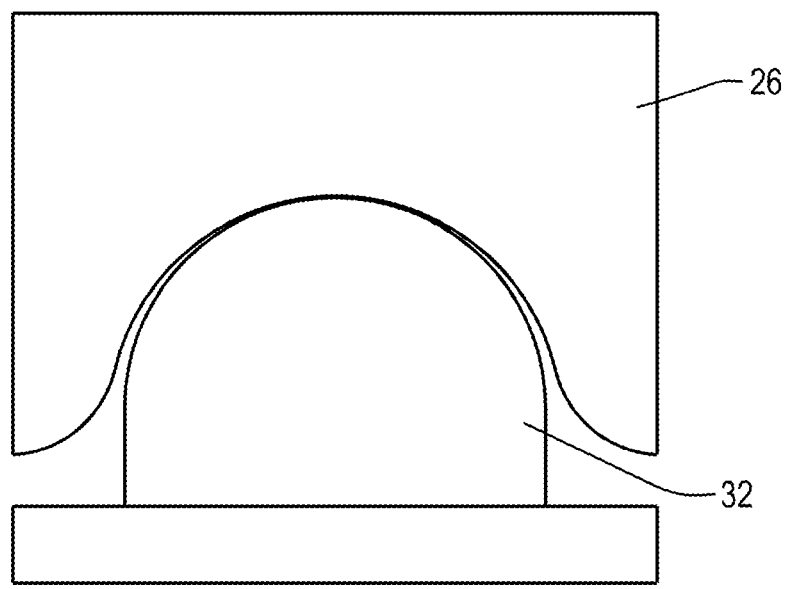
FIG. 6 represents a ball and top plate joint of the type used in the structural assembly of FIG. 1.

The foot portion 20 includes oppositely-disposed anterior and posterior ends defined by a base 30, and a protrusion 32 (FIG. 4) that protrudes from a first (upper) surface 33A of the base 30 adjacent the posterior end of the foot portion 20. The protrusion 32 has a semispherical or hemispherical upper surface. Preferably, the base 30 includes an arcuate region in a second (lower) surface 33B between its anterior and posterior ends to define an arch that approximates a normal arch of a human foot. In addition, an edge of the foot portion 20 closest to the toe portion 22 is preferably shaped to mimic the slant of a human's toes to simulate a similar force distribution. The top plate 26 (FIGS. 4 and 5) is a rectangular cuboid-like component having a recess on a lower side thereof configured to overlay and couple with the upper surface of the protrusion 32. The recess in the top plate 26 preferably has a semispherical or hemispherical shape that is complementary to the semispherical or hemispherical upper surface of the protrusion 32 (generally as represented in FIG. 6). The cover plate 24 is also a rectangular cuboid-like component having a cavity on a lower side thereof that is configured to accommodate the top plate 26, up to and including the entirety of the top plate 26 (generally as represented in FIGS. 2 and 3). The foot portion 20 is coupled to the cover plate 24 and top plate 26 to function as an ankle joint. In particular, both the top plate 26 and cover plate 24 include rounded through-holes 36 and 34 that are aligned with a vertically-elongated lateral passage 42 that passes entirely through the protrusion 32 of the foot portion 20. The top plate 26 and cover plate 24 are pivotally connected to the foot portion 20 with a cylindrical rod or bolt 38 that passes through the through-holes 34 and 36 in the top plate 26 and cover plate 24 and through the lateral passage 42 in the protrusion 32 of the foot portion 20, and is secured therein with a nut 39. Optionally, one or more of the components may have features that promote manufacturing of the components. For example, the foot portion 20 includes holes 76 that are used to secure the foot portion 20 to a fixture when machining the bottom part of the foot portion 20, but otherwise are not functional in the final device 10.

The foot portion 20 is free to pivot about the bolt 38 and is therefore capable of dorsiflexion and plantarflexion relative to the cover plate 24 and the top plate 26, in other words, upward and downward movements at the anterior end of the foot portion 20. In addition, the elongated profile of the passage 42 permits the bolt 38 to move vertically within the passage 42, allowing the foot portion 20 to be capable of limited pronation and supination (side-to-side (lateral) movements) relative to the cover plate 24 and the top plate 26. The top plate 26 and the cover plate 24 are stabilized or fixed relative to one another, for example, with pins 40 that are located in holes 42 on a top surface of the top plate 26 and holes 44 within the cavity of the cover plate 24, as best seen in FIG. 5.

The cover plate 24 includes a hole 46 through which a fastener 48 protrudes. The fastener 48 is configured to be secured to a prosthetic attachment device for coupling the ankle and foot prosthetic device 10 to an individual. The fastener 48 may be secured to the cover plate 24 or, as represented in FIG. 5, may have a head that is located between the cover plate 24 and top plate 26 and effectively secured therein. Alternatively, the fastener 48 may be an integral component of the cover plate 24. The toe portion 22 is pivotally coupled to the anterior end of the foot portion 20 with a hinge 50, and is secured thereto with fasteners such as bolts 52 and nuts 54.

Figure 7:
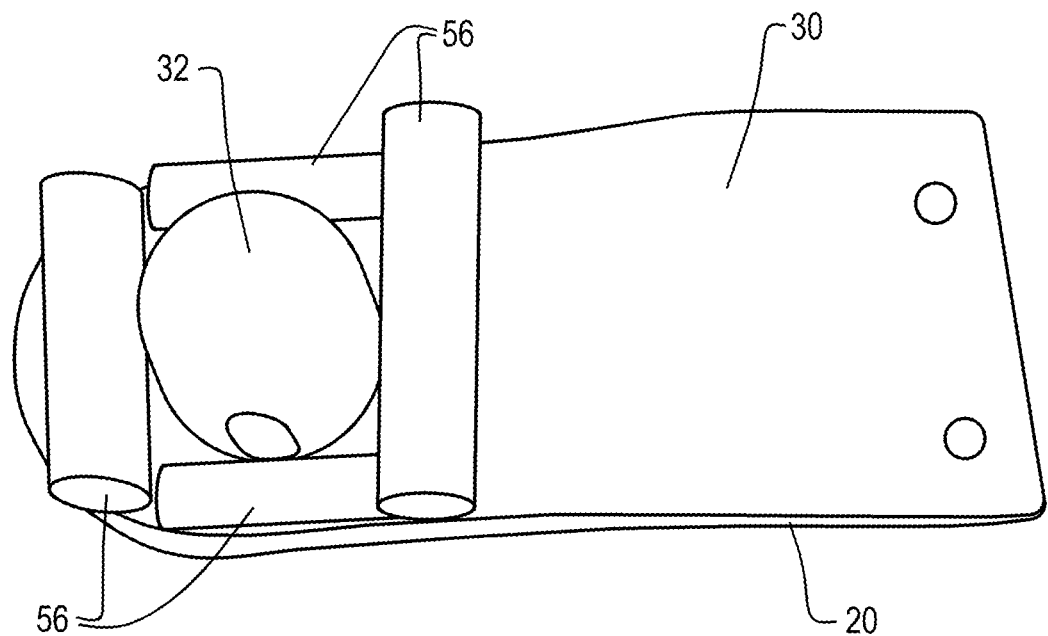
FIG. 7 shows the foot portion of the structural assembly of FIG. 1 as further comprising rubber rods thereon.
Figure 8:
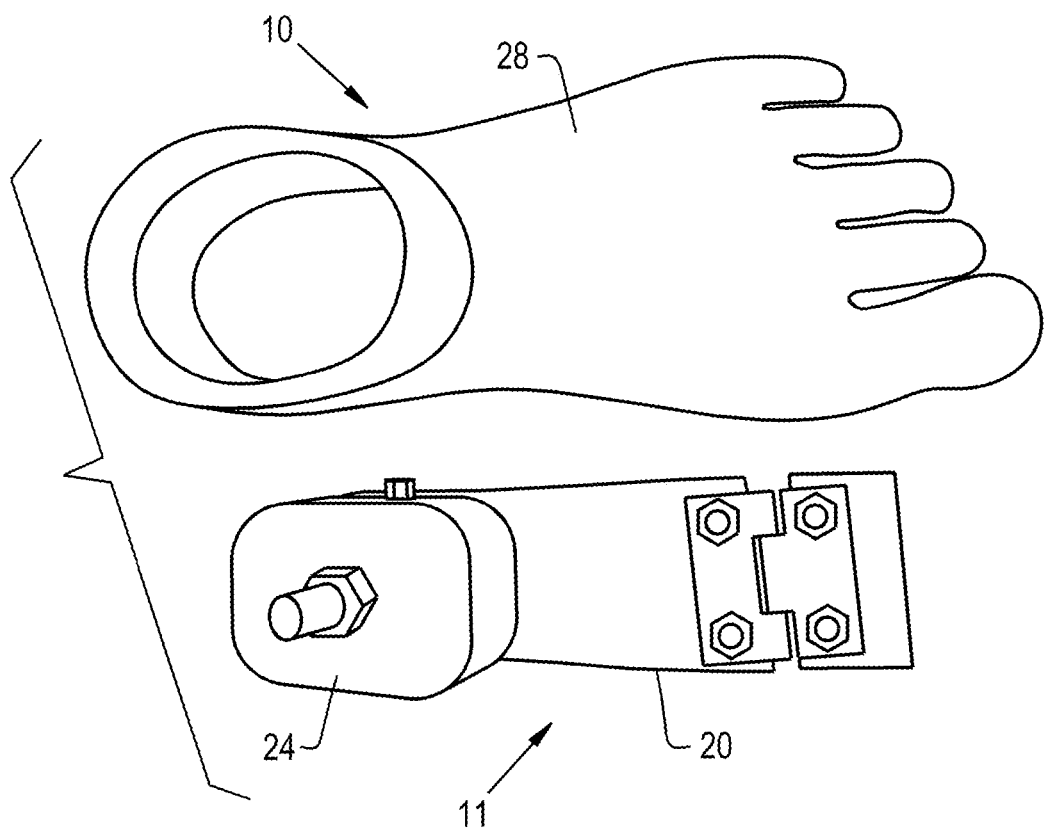
FIG. 8 shows the structural assembly and the foot shell of FIG. 1.

Preferably, the device 10 includes means for controlling or restricting movement of the ankle joint formed by the foot portion 20, cover plate 24, and top plate 26. For example, FIG. 7 depicts a prototype of the ankle and foot prosthetic device 10, and represents the foot portion 20 as comprising rubber rods 56 attached to a top surface of the foot portion 20 and surrounding the protrusion 32. The rods 56 are configured to contact the cover plate 24 and/or top plate 26 in order to provide elastic resistance to motion of the foot portion 20 relative thereto, and therefore provide some elastic resistance to dorsiflexion, plantarflexion, pronation, and supination. By restricting the motion of the foot portion 20 relative to the cover plate 24 and/or top plate 26, the device 10 may be configured to more accurately mimic the normal ankle movement range of a human ankle. It is foreseeable that the individual rods 56 may be configured to provide relatively different amounts of resistance to motion, for example by having different durometers, in order to limit the range of motion more in one direction than another. Further, it is foreseeable that individual users may require custom combinations of rods 56 that are each individually tailored to provide amounts of resistance specific to the user in order to mimic the normal motion specific to the user. Whereas rods 56 are shown, a wide range of components could be employed to provide an elastic or biasing functionality.

Figure 9:
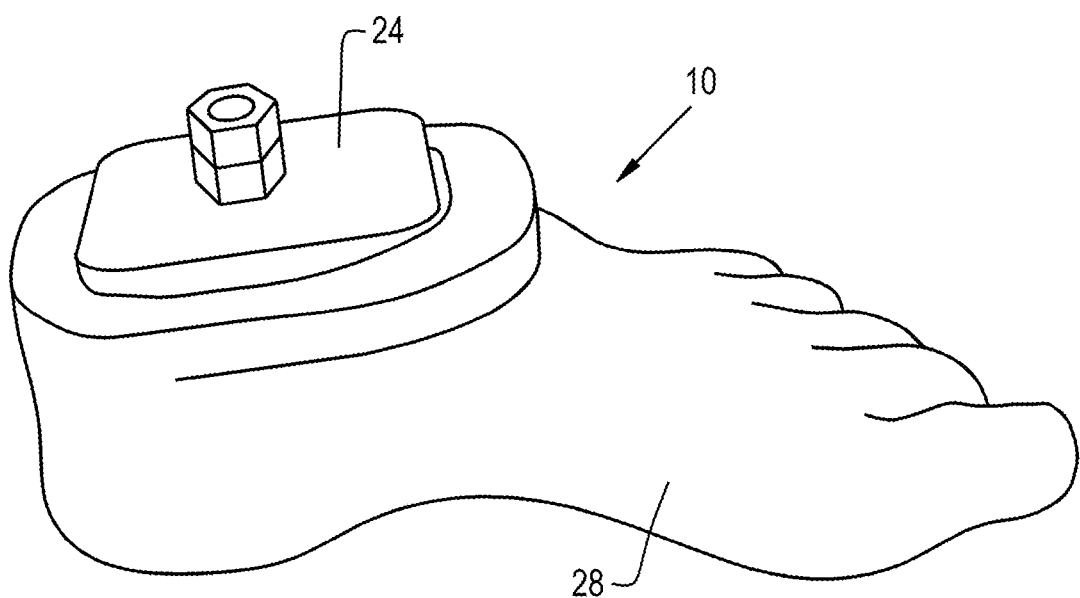
FIG. 9 shows the structural assembly of FIG. 8 inserted into the foot shell of FIG. 8.
Figure 25:
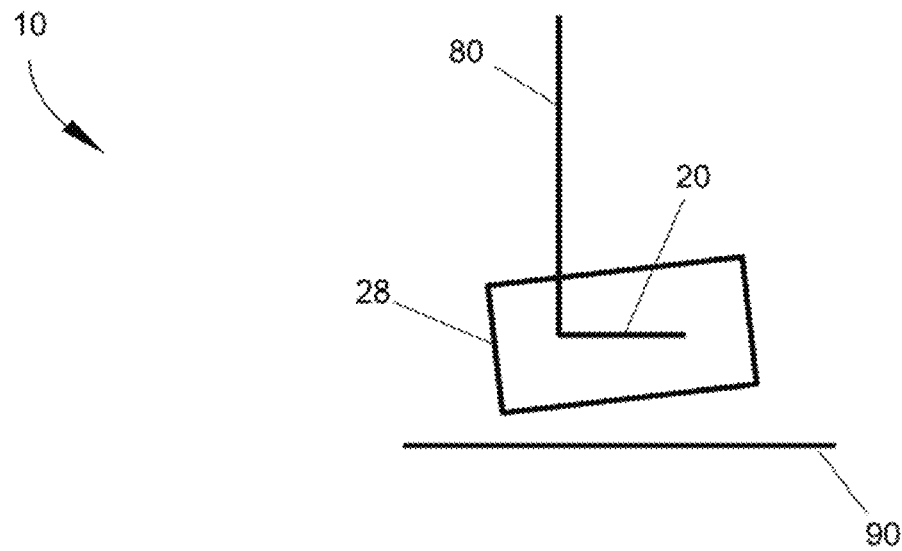
FIGS. 25 and 26 schematically represent prosthetic devices with an inclined at-rest position in accordance with nonlimiting embodiments of the invention.
Figure 26:
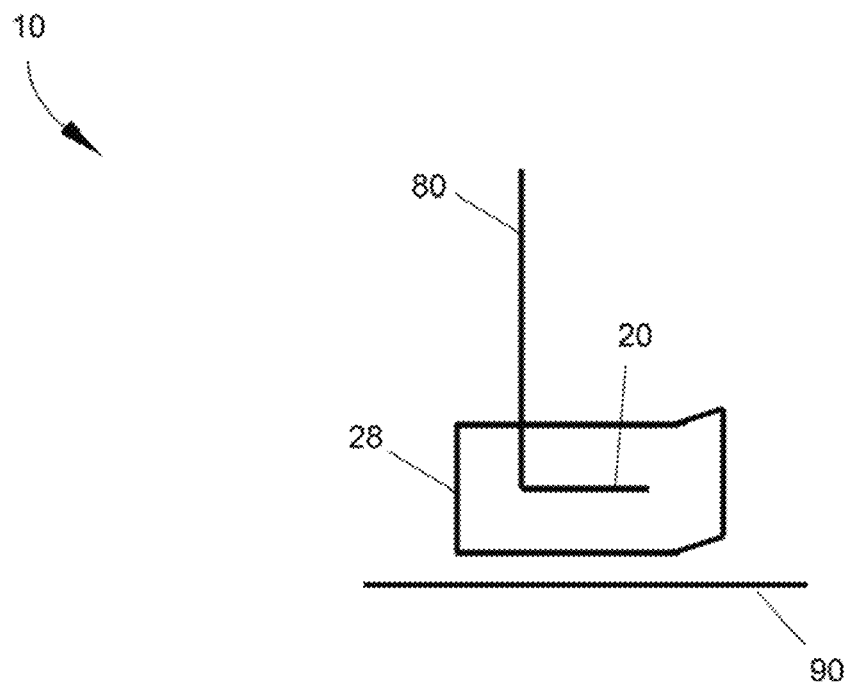

As represented in FIGS. 1 and 9, the foot portion 20 is configured to be located within the foot shell 28 during use of the device 10. The foot shell 28 provides a protective exterior layer that may improve the durability of the structural assembly 11. In addition, the shell 28 preferably biases the foot shell 28 only, or the foot portion 20 and the foot shell 28 in an inclined position relative to ground, in other words, in a dorsiflexion position. This is in contrast to conventional prosthetic devices that provide a foot portion that is fixed at an angle of ninety degrees to a leg portion of the device or oriented parallel to ground. With such conventional configurations, users often trip over the toe portion of the device when walking, because the users do not have the ability to flex the foot portion of the device while walking as non-amputees do with their feet. By angling the "at-rest" position of the foot portion 20 and foot shell 28 to an inclined position, the toe portion is less likely to make contact with the ground when a user is walking. Preferably, the foot shell 28 only, or foot portion 20 and foot shell 28 are inclined by about three to ten degrees from ground, that is, oriented about eighty-seven to eighty degrees relative to the fastener 48 (assuming the fastener 48 is parallel to the leg portion of a prosthetic attachment device). When wearing shoes, a total "at-rest" position of the foot portion 20 and foot shell 28 during use is a combination of the bias applied by the foot shell 28 and the padding in the heel of a shoe in which the device 10 is located. For example, athletic shoes commonly include a heel that inclines a foot by about five to seven degrees. Therefore, the foot portion 20 and foot shell 28 may be biased to an incline of about three degrees, such that when located within an athletic shoe, the foot portion 20 and foot shell 28 have a total "at-rest" position that is inclined by about eight to ten degrees, which is believed to be preferred for athletic activities. FIG. 25 represents a first nonlimiting embodiment wherein the foot portion 20 forms a ninety-degree angle with a leg portion 80 when the device 10 is located above a surface 90 with none on the user's weight distributed on the device 10, and the foot shell 28 forms an inclined at-rest position. This may be accomplished, for example, by providing a slot within the foot shell 28 for receiving the foot portion 20 that is declined downwardly (plantarflexion). In this embodiment, when the user stands still and puts weight on the device 10, it is foreseeable and within the scope of the invention that the foot portion 20 may still form about a ninety-degree angle with a leg portion 80 due to posterior portions of the foot shell 28 compressing under the load. FIG. 26 represents an alternative nonlimiting embodiment wherein only an anterior portion of the foot shell 28 is inclined. It is also foreseeable that the foot portion 20 could be biased in the inclined "at-rest" position relative to the cover plate 24 and top plate 26 by means other than the foot shell 28.

In addition to the above functions, the foot shell 28 preferably provides elastic resistance to the toe portion 22 such that the hinge 50 is limited in its pivoting range and thereby better mimics the movement range of human toes. Preferably, the foot shell 28 provides sufficient elastic resistance such that the toe portion 22 has a maximum bending angle relative to the foot portion 20 of forty-five degrees or less. Alternatively, it is foreseeable that the device 10 may include additional means for biasing the toe portion 22 or hinge 50 that is capable of limiting the maximum bending angle relative to the foot portion 20 of the toe portion 22 to about forty-five degrees or less, either alone or in combination with the foot shell 28.

Figure 10:
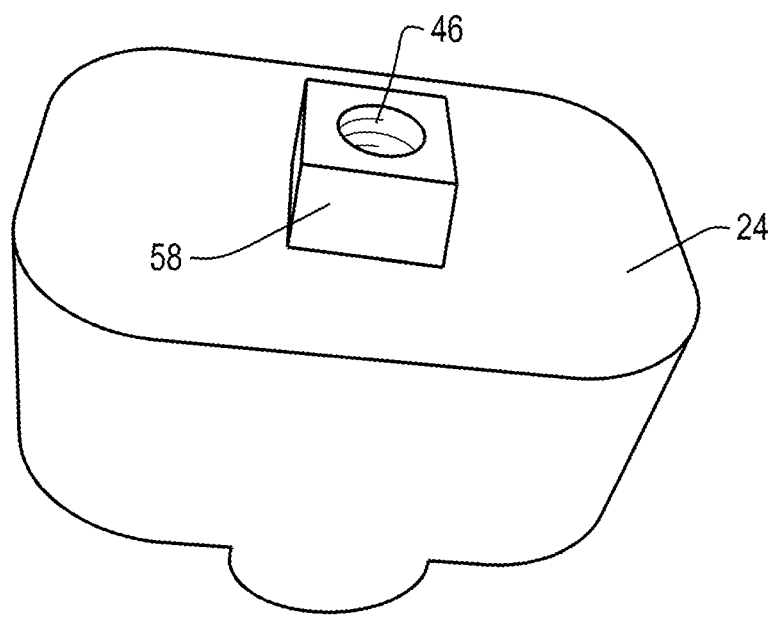
FIGS. 10 and 11 show a cover plate and an attachment device which in combination form a key and hole locking system of the structural assembly.
Figure 11:
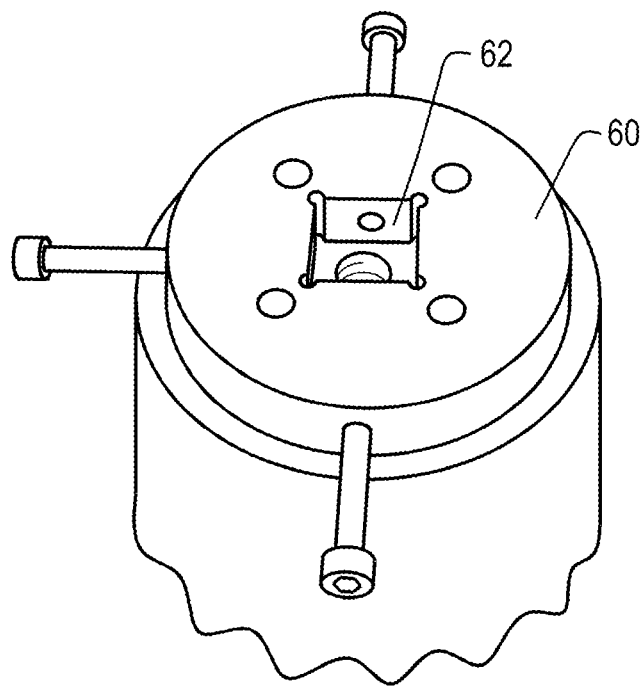

In order to preventing the device 10 from rotating in a horizontal plane when connected to a prosthetic attachment device, the cover plate 24 may include a key and hole feature, such as but not limited to, the addition of a raised protrusion shaped to match a recess of the attachment device. For example, FIG. 10 represents the cover plate 24 as including a cubic-shaped protrusion 58 that is complementary to a recess 62 in an attachment device 60 represented in FIG. 11. Alternatively, if the attachment device 60 were to include a pyramid attachment, the pyramid attachment may be secured to the cover plate 24 and/or top plate 26 and the key and hole system may be unnecessary.

Figure 12:
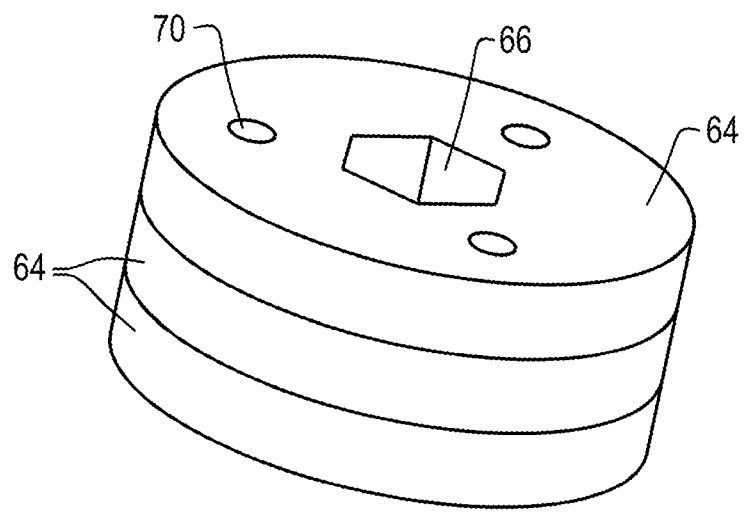
FIGS. 12 and 13 represent assembled and exploded views of shimming plates in accordance with a nonlimiting aspect of the invention.
Figure 13:
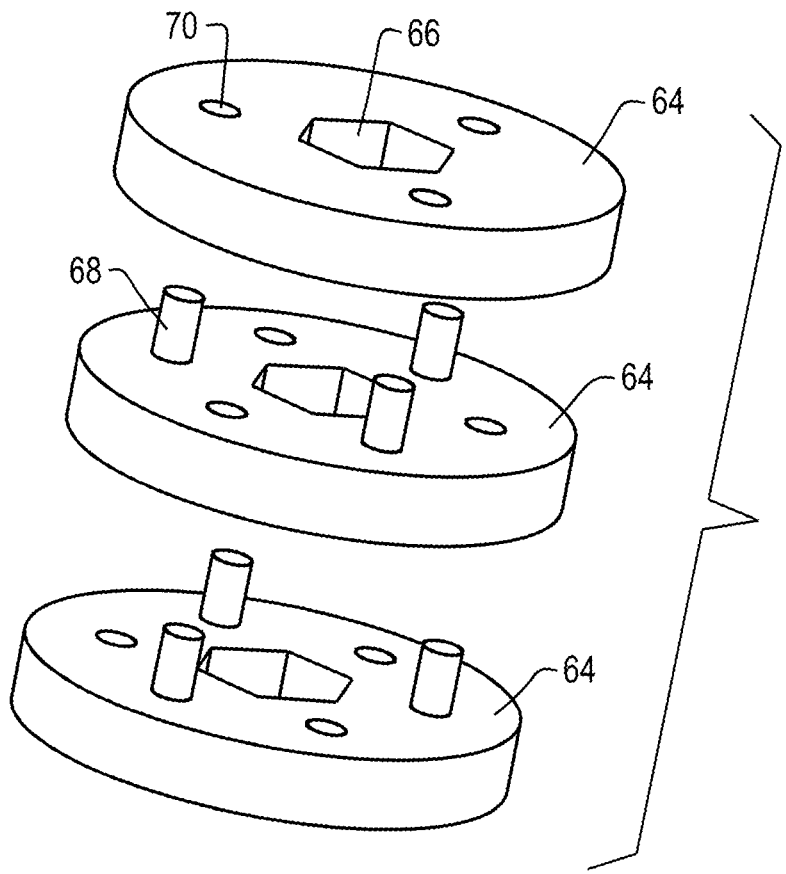

FIGS. 12 and 13 represent shimming plates 64 that can be placed between the cover plate 24 and an attachment device to accommodate the height for an individual user by modifying the vertical height of the device 10. FIGS. 12 and 13 represent the shimming plates 64 as configured to be used in conjunction with a cover plate 24 having a key and hole feature that includes a protrusion 58 with a hexagonal-shaped cross-section. The fastener 48 securing the device 10 to a prosthetic attachment device can be routed through hexagonal-shaped holes 66 in the shimming plates 64 to engage a prosthetic attachment device. If more than one shimming plate 64 is used, pins 68 and holes 70 between the plates 64 prevent rotation between the plates 64. Each shimming plate 64 may be rotatably fixed relative to one another with the pins 68.

The components of the device 10 may be formed from various materials. For example, the foot portion 20, toe portion 22, and cover plate 24 may be formed of a metallic or composite material capable of supporting loads applied by a user during use while providing sufficient durability to ensure a minimum desired operating life for the device 10, for example, five years. According to a nonlimiting example, the cover plate 24, foot portion 20, and toe portion 22 may be formed of aluminum or an alloy thereof. According to another nonlimiting example, the foot portion 20 may be a carbon fiber composite material. The top plate 26 generally functions as a barrier between the protrusion 32 of the foot portion 20 and the cover plate 24 to prevent wear on these components. As such, the top plate 26 is preferably formed of a material that has a relatively low coefficient of friction and high wear resistance. According to a nonlimiting example, the top plate 26 can be formed of ultra-high molecular weight polyethylene. The foot shell 28 is preferably formed of a material capable of applying elastic resistance to the toe portion 22 to limit its maximum bending angle, yet is sufficiently deformable such that the structural assembly 11 may be inserted therein, and has a relatively low cost such that the foot shell 28 may be replaced as necessary due to wear from use. According to a nonlimiting example, the foot shell 28 can be formed of a polymeric material, such as but not limited to, urethane.

Figure 14:
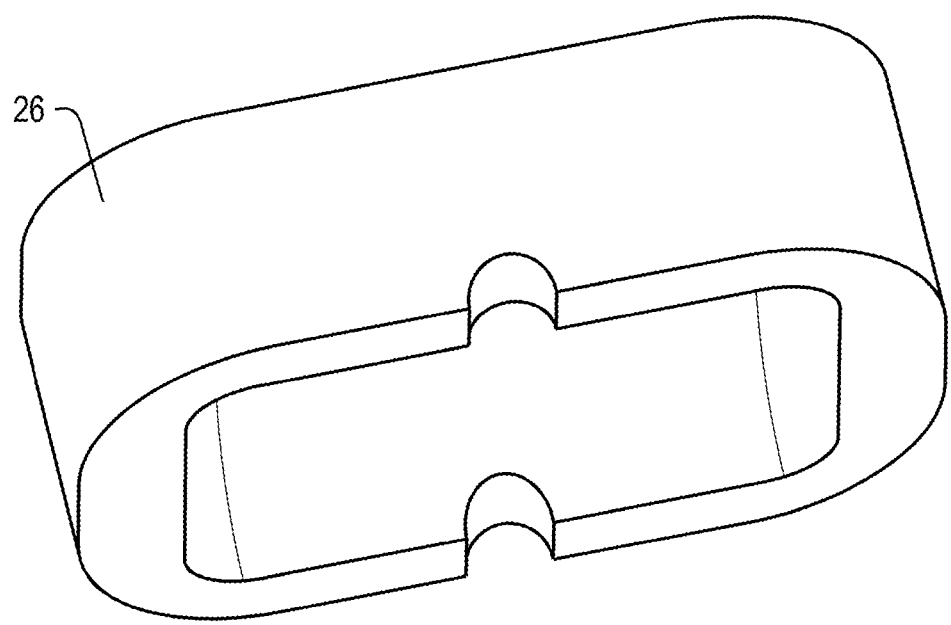
FIG. 14 is a perspective view representing an alternative embodiment of a top plate.
Figure 15:
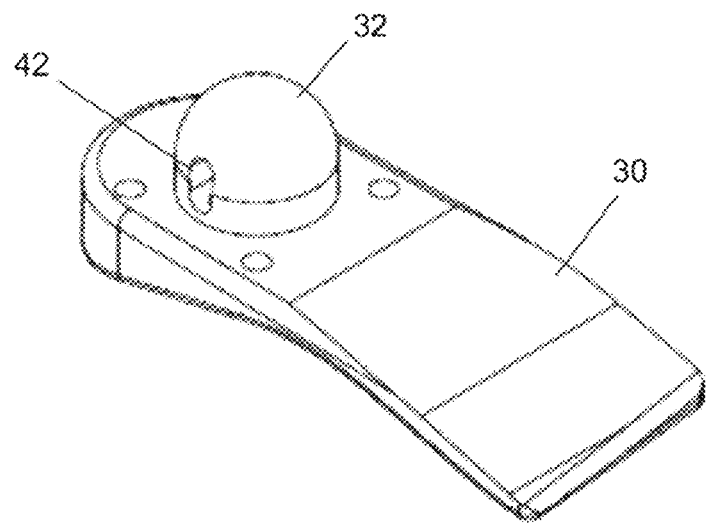
FIGS. 15 through 18 depict various views showing in isolation nonlimiting embodiments of a foot portion, toe portion, top plate, and cover plate, respectively, of the structural assembly of FIGS. 1 through 4.
Figure 16:
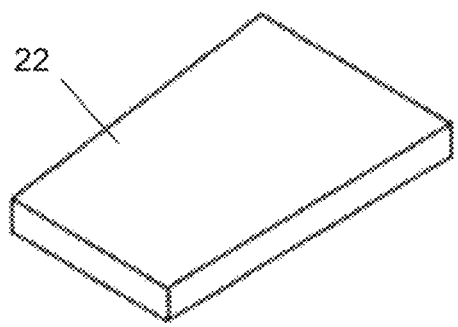
Figure 17:
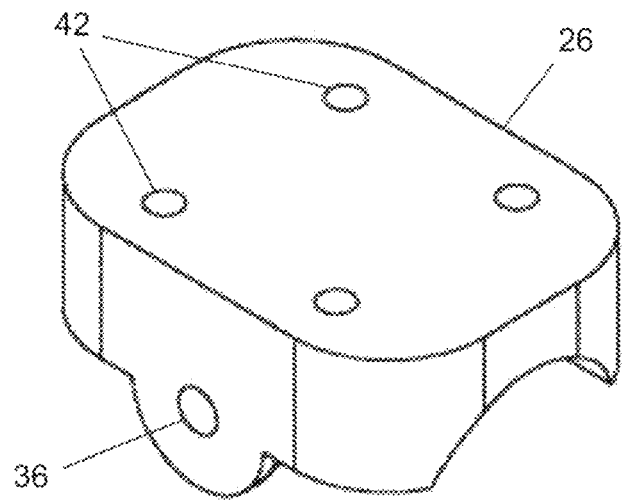
Figure 18:
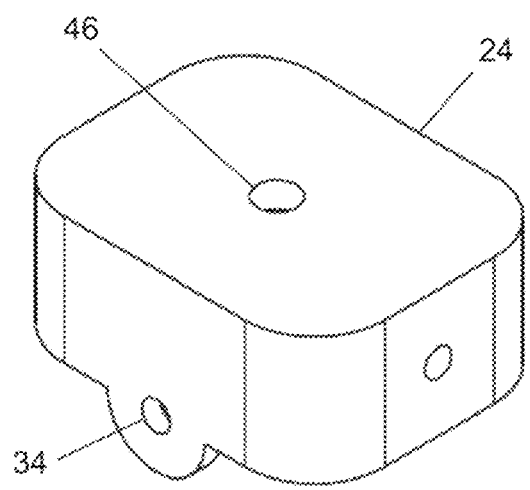
Figure 19:
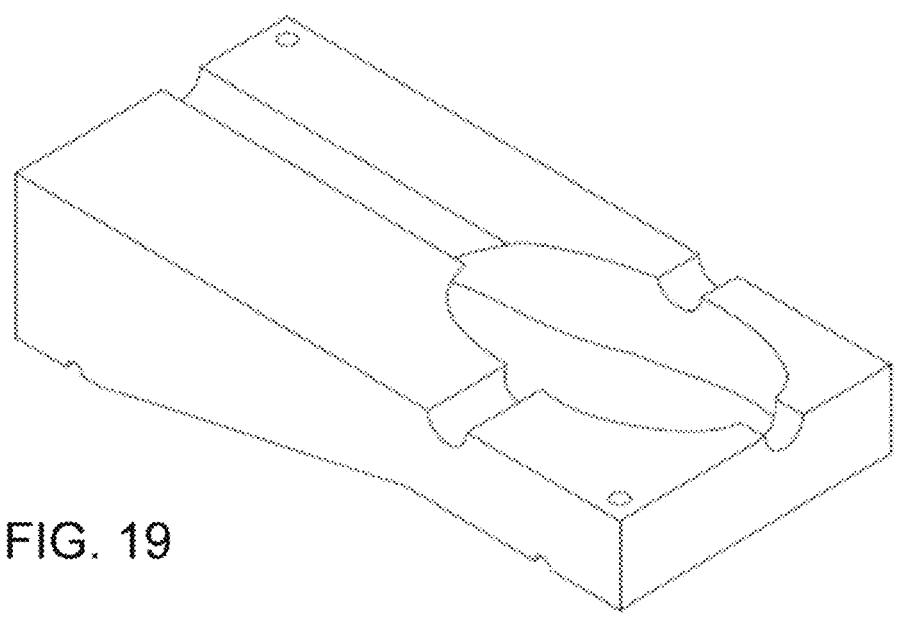
FIGS. 19 through 22 represent various views of nonlimiting components for producing a foot shell, including a bottom mold, a top mold, a mold core, and a mold cross (for positioning the core).
Figure 20:
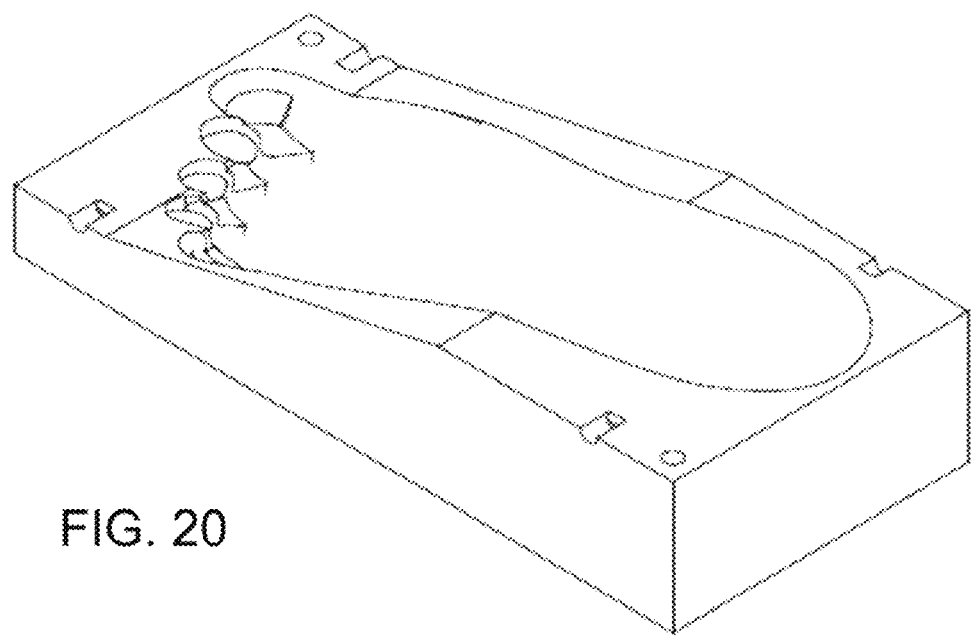
Figure 21:
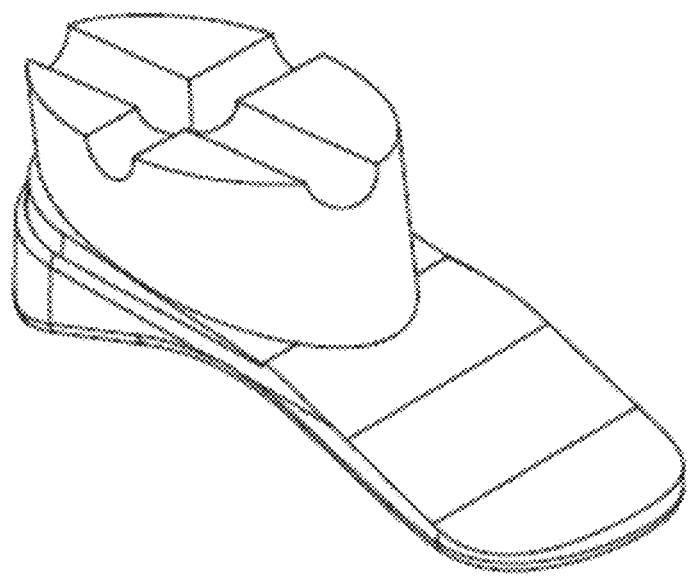
Figure 22:
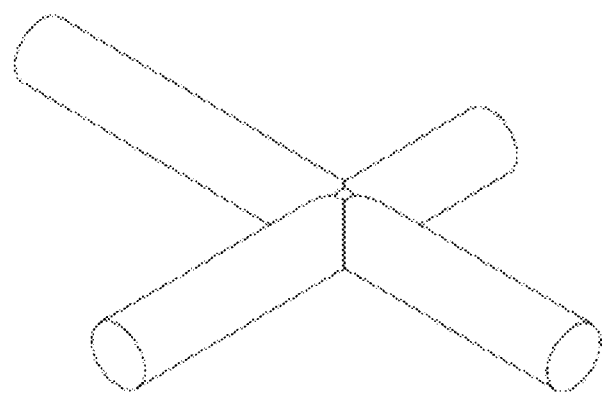

Various modifications to the components of the device 10 are foreseeable and within the scope of the invention. Such modifications may be made to reduce the overall weight of the device 10, since prosthetic weight is a common complaint among amputees. For example, holes can be created in individual components in order to reduce the total weight of the device 10. As another example, FIG. 14 represents the top plate 26 as being shorter so that the through-holes 36 have been replaced by arcuate notches intended to engage but not surround the bolt 38. Such modification may be implemented if the cover plate 24 provides sufficient strength to safely secure an attachment device to the bolt 38. Additionally, fillets may be added to the corners of the toe portion 22 in order to reduce wear on the foot shell 28 over time.

When worn by a user, the device 10 represented by FIGS. 1 through 9 can be secured to the user via a known prosthetic attachment device, and a conventional shoe may be worn over the shell 28 of the device 10.

Figure 23:
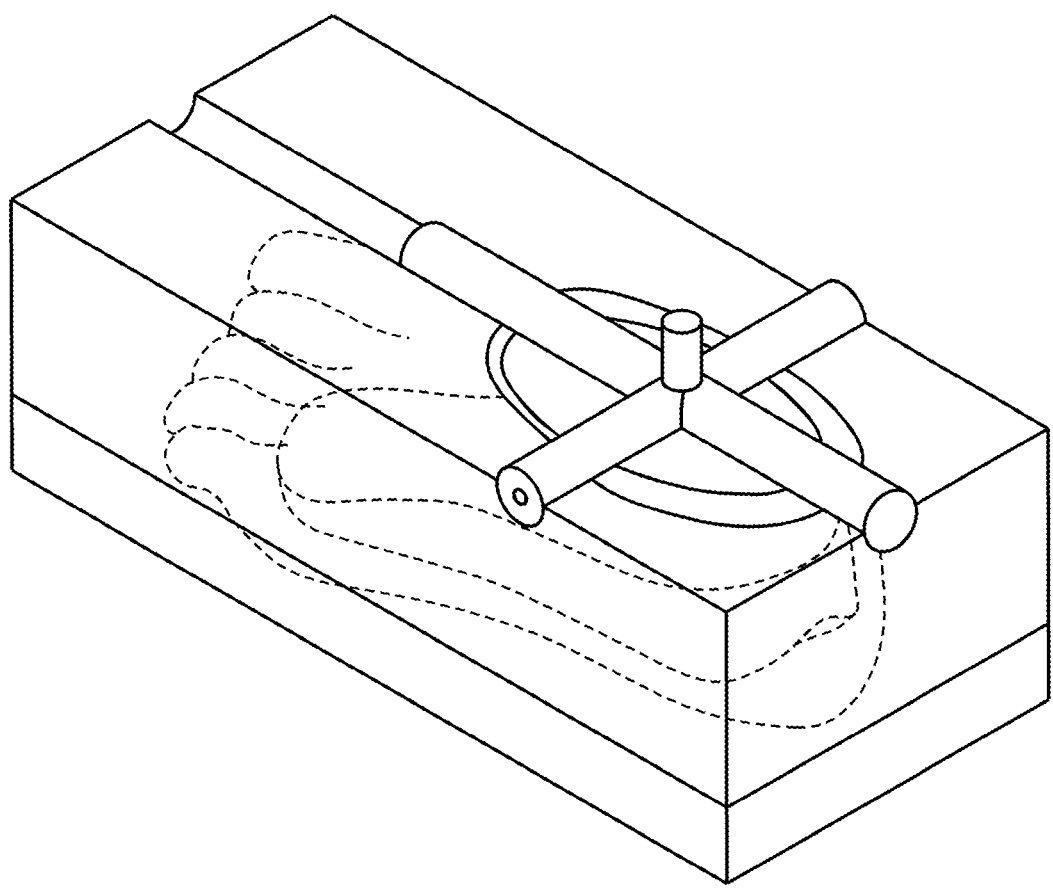
FIG. 23 represents a mold assembly comprising the components of FIGS. 19 through 22.

FIGS. 15 through 18 depict additional views of nonlimiting embodiments of the foot portion 20, toe portion 22, top plate 26, and cover plate 24, respectively, of FIGS. 1 through 9. FIGS. 19 through 22 represent perspective views of a nonlimiting mold for producing the foot shell 28, including a top mold (FIG. 19), a bottom mold (FIG. 20), a mold core (FIG. 21), and a mold cross (FIG. 22) for positioning the core. FIG. 23 represents a mold assembly comprising the components of FIGS. 19 through 22.

Figure 27:
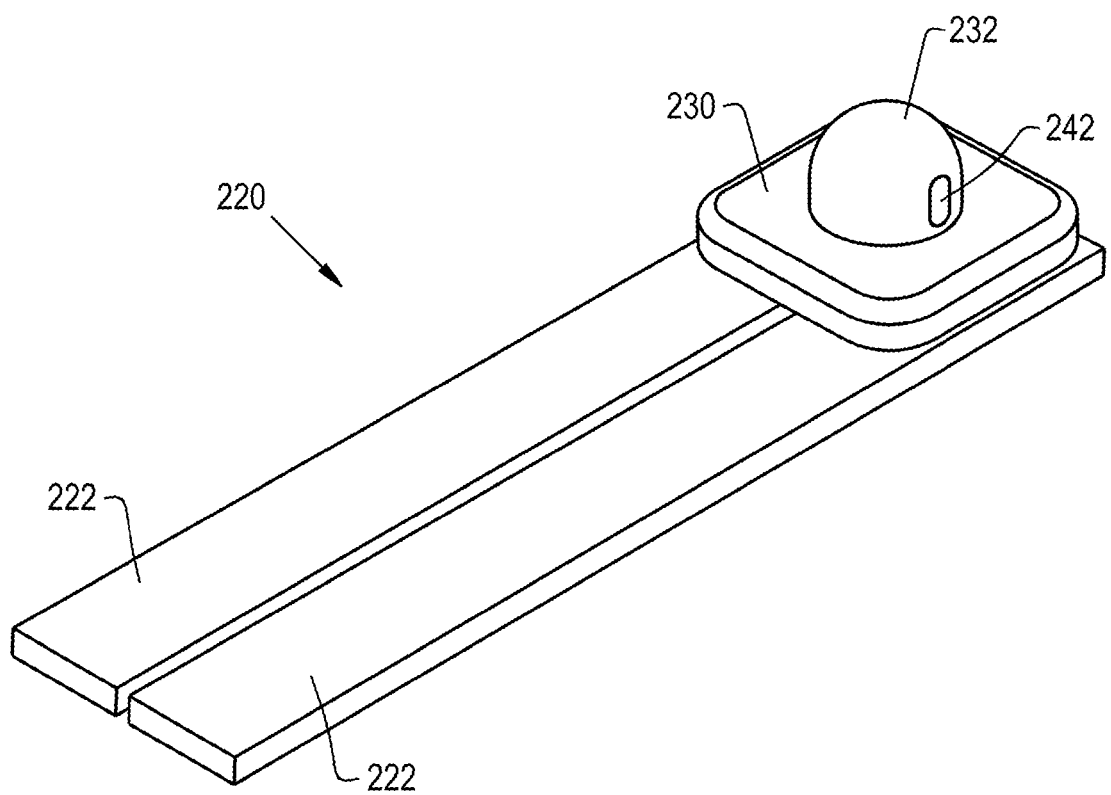
FIG. 27 represents a second nonlimiting foot portion suitable for replacing the foot and toe portions of the structural assembly of FIGS. 1 through 4.

FIG. 27 schematically represents a second nonlimiting embodiment, wherein the foot portion 20 and the toe portion 22 of the internal structural assembly 11 of the device 10 are replaced with a split-toe foot portion 220. The foot portion 220 includes a base 230 and a protrusion 232 that protrudes from an upper surface of the base 230 adjacent the posterior end of the foot portion 220. The protrusion 232 has a semispherical or hemispherical upper surface and includes a lateral passage 242. At least two toe portions 222 are secured to a lower surface of the base 230 and extend in toward the anterior direction of the foot portion 220. The foot portion 220 may be assembled with the top plate 26, cover plate 24, and foot shell 28 shown in the preceding drawings to interact therewith in substantially the same manner as described above in relation to the foot portion 20 and the toe portion 22. Further, any of the aspects of the invention discussed in relation to FIGS. 1 through 26 may be applicable to the foot portion 220 of FIG. 27.

For example, the device 10 including the foot portion 220 may include means for controlling or restricting movement of the ankle joint formed by the foot portion 220, cover plate 24, and top plate 26, such as but not limited to including the rubber rods 56 attached to a top surface of the foot portion 220 and surrounding the protrusion 232. The shell 28 may bias the foot shell 28 only, or the foot portion 220 and the foot shell 28 in a dorsiflexion position.

Although the foot portion 220 may be formed of any of the materials discussed above in relation to the foot portion 20, the toe portions 222 are preferably formed of a material that allows the toe portions 222 to independently flex at least in the dorsiflexion direction when a load is applied thereto. This movement is preferably limited to about forty-five degrees or less, either alone or in combination with the foot shell 28. Such limitations on the flexing of the toe portions 222 may be due to the material from which they are formed, resistance applied by the foot shell 28 or any other biasing means, or a combination thereof.

While the invention has been described in terms of specific or particular embodiments, it should be apparent that alternatives could be adopted by one skilled in the art. For example, the physical configuration of the device 10 and its components could differ from that shown, and materials and processes/methods other than those noted could be used. As a particular example, the roles of the cover plate 24 and top plate 26 could be served by a single component or by more than two separate components, all of which may constitute a "plate portion" that couples the foot portion 20 or 220 to a prosthetic attachment device. In addition, the invention encompasses additional or alternative embodiments in which one or more features or aspects of a particular embodiment could be eliminated or two or more features or aspects of different disclosed embodiments could be combined. Accordingly, it should be understood that the invention is not necessarily limited to any embodiment described herein or illustrated in the drawings. It should also be understood that the phraseology and terminology employed above are for the purpose of describing the disclosed/illustrated embodiments, and do not necessarily serve as limitations to the scope of the invention. Therefore, the scope of the invention is to be limited only by the following claims.

The invention claimed is:

1. A device for use as a prosthetic foot, the device comprising:

a foot portion having anterior and posterior ends, a first surface, and a protrusion that protrudes from the first surface adjacent the posterior end of the foot portion, the foot portion further having a second surface oppositely-disposed from the first surface, the protrusion having an upper surface that has a semispherical or hemispherical shape, and the protrusion having a passage therethrough extending laterally relative to the foot portion;

a plate portion configured to couple the device to an attachment device and thereby be functionally secured to a user, the plate portion having a recess on a lower side thereof that overlays and is coupled with the upper surface of the protrusion, and the recess having a lower surface that has a semispherical or hemispherical shape, wherein the upper surface of the protrusion and the lower surface of the recess are complementarily convex and concave;

a cylindrical rod located within the passage of the protrusion and having ends protruding therefrom on oppositely-disposed lateral sides of the protrusion, wherein the plate portion is pivotally coupled to the ends of the rod on oppositely-disposed lateral sides of the protrusion to enable movement of the foot portion in dorsiflexion and plantarflexion directions of the device relative to the plate portion and the passage in the protrusion of the foot portion being elongate in the direction between the first and second surfaces to enable movement of the foot portion in pronation and supination directions of the device relative to the plate portion; and at least one elastic component disposed adjacent the oppositely-disposed lateral sides of the protrusion and adjacent oppositely-disposed anterior and posterior sides of the protrusion so as to:

contact the first surface of the foot portion and oppositely-disposed anterior and posterior portions of the plate portion on oppositely-disposed anterior and posterior sides of the recess in the plate portion to elastically resist movement of the foot portion relative to the plate portion when the foot portion moves in the dorsiflexion and plantarflexion directions relative to the plate portion; and contact the first surface of the foot portion and oppositely-disposed lateral portions of the plate portion on oppositely-disposed lateral sides of the recess in the plate portion to elastically resist movement of the foot portion relative to the plate portion when the foot portion moves in the pronation and supination directions relative to the plate portion.

2. The device of claim 1, wherein the device further includes a toe portion pivotally coupled to the anterior end of the foot portion, and the toe portion is elastically limited to a maximum angle relative to the foot portion of forty-five degrees or less.

3. The device of claim 1, wherein the foot portion has a dorsiflexion at-rest position.

4. The device of claim 1, wherein at least the foot portion is covered in a removable protective shell.

5. The device of claim 1, wherein the device further includes a toe portion that is pivotally coupled to the anterior end of the foot portion and elastically resists pivoting relative to the foot portion.

6. The device of claim 1, wherein the foot portion is a split-toe foot portion that comprises at least two elongated members.

7. The device of claim 6, wherein the elongated members define toe portions at the anterior end of the foot portion and the toe portions are flexible in the dorsiflexion direction relative to the posterior end of the foot portion.

8. The device of claim 1, wherein the plate portion comprises:
a cover plate configured to couple to the attachment device; and
a top plate having the recess configured to couple with the semispherical or hemispherical surface of the protrusion of the foot portion, the top plate being located between the protrusion and the cover plate.

9. A system for use as a lower leg prosthetic, the system comprising:
an attachment device configured to be secured to a user;
a foot portion having anterior and posterior ends, a first surface, and a protrusion that protrudes from the first surface adjacent the posterior end of the foot portion, the foot portion further having a second surface oppositely-disposed from the first surface, the protrusion having an upper surface that has a semispherical or hemispherical shape, and the protrusion having a passage therethrough extending laterally relative to the foot portion;
a toe portion located at the anterior end of the foot portion;
a plate portion configured to couple to the attachment device, the plate portion having a recess on a lower side thereof that overlays and is coupled with the upper surface of the protrusion, the recess having a lower surface that has a semispherical or hemispherical shape, wherein the upper surface of the protrusion and the lower surface of the recess are complementarily convex and concave;
a cylindrical rod located within the passage of the protrusion and having ends protruding therefrom on oppositely-disposed lateral sides of the protrusion, wherein the plate portion is pivotally coupled to the ends of the rod on oppositely-disposed lateral sides of the protrusion to enable movement of the foot portion in dorsiflexion and plantarflexion directions of the device relative to the plate portion and the passage in the protrusion of the foot portion being elongate in the direction between the first and second surfaces to enable movement of the foot portion in pronation and supination directions of the device relative to the plate portion; and
at least one elastic component disposed adjacent the oppositely-disposed lateral sides of the protrusion and adjacent oppositely-disposed anterior and posterior sides of the protrusion so as to:
contact the first surface of the foot portion and oppositely-disposed anterior and posterior portions of the plate portion on oppositely-disposed anterior and posterior sides of the recess in the plate portion to elastically resist movement of the foot portion relative to the plate portion when the foot portion moves in the dorsiflexion and plantarflexion directions relative to the plate portion; and
contact the first surface of the foot portion and oppositely-disposed lateral portions of the plate portion on oppositely-disposed lateral sides of the recess in the plate portion to elastically resist movement of the foot portion relative to the plate portion when the foot portion moves in the pronation and supination directions relative to the plate portion.

10. The system of claim 9, wherein the toe portion is pivotally coupled to the foot portion and elastically limited to a maximum angle relative to the foot portion of forty-five degrees or less in the dorsiflexion direction.

11. The system of claim 9, wherein the foot portion has a dorsiflexion at-rest position of less than ninety degrees relative to a longitudinal axis of the plate portion.

12. The system of claim 9, wherein at least the foot portion and the toe portion are covered in a removable protective shell.

13. The system of claim 12, wherein the protective shell resists movement of the foot portion in the dorsiflexion, plantarflexion, pronation, and/or supination directions relative to the plate portion.

14. The system of claim 9, wherein the toe portion is pivotally coupled to the foot portion and elastically resists pivoting relative to the foot portion in the dorsiflexion direction.

15. The system of claim 9, wherein the foot portion is a split-toe foot portion that comprises at least two elongated members.

16. The device of claim 15, wherein the elongated members define the toe portion and at least a second toe portion that are flexible in the dorsiflexion direction relative to the posterior end of the foot portion.

17. The system of claim 9, wherein the plate portion comprises:
a cover plate configured to couple to the attachment device; and
a top plate having the recess configured to couple with the semispherical or hemispherical surface of the protrusion of the foot portion, the top plate being located between the protrusion and the cover plate.

* * * * *